(12) United States Patent
Meridew

(10) Patent No.: US 9,820,853 B2
(45) Date of Patent: Nov. 21, 2017

(54) ACETABULAR CUP SYSTEM

(75) Inventor: Jason D. Meridew, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 1177 days.

(21) Appl. No.: 12/436,225

(22) Filed: May 6, 2009

(65) Prior Publication Data

US 2010/0286789 A1  Nov. 11, 2010

(51) Int. Cl.
*A61F 2/32* (2006.01)
*A61F 2/34* (2006.01)
*A61F 2/30* (2006.01)

(52) U.S. Cl.
CPC .......... *A61F 2/32* (2013.01); *A61F 2/34* (2013.01); *A61F 2002/30004* (2013.01); *A61F 2002/30014* (2013.01); *A61F 2002/30616* (2013.01); *A61F 2250/0014* (2013.01); *A61F 2250/0018* (2013.01)

(58) Field of Classification Search
CPC .......... A61F 2/32; A61F 2/30942; A61F 2/34; A61F 2/36; A61F 2/4609; A61F 2/3609; A61F 2/4607; A61F 2002/30607; A61F 2002/30616; A61F 2002/30649; A61F 2/3859; A61F 2/4014
USPC ............................................. 623/22.11–22.4
See application file for complete search history.

(56) References Cited

U.S. PATENT DOCUMENTS

| 4,519,101 A | 5/1985 | Schreiber et al. |
| 4,808,186 A * | 2/1989 | Smith .................. A61F 2/3662 606/63 |
| 4,828,565 A | 5/1989 | Duthoit et al. |
| 4,834,759 A | 5/1989 | Spotorno et al. |
| 4,961,748 A | 10/1990 | Frey et al. |
| 5,062,853 A * | 11/1991 | Forte .......................... 623/22.2 |
| 5,074,881 A | 12/1991 | Thull et al. |
| 5,108,448 A | 4/1992 | Gautier |
| 5,507,828 A | 4/1996 | Maumy et al. |

(Continued)

FOREIGN PATENT DOCUMENTS

| DE | 202008008565 U1 | 8/2008 |
| FR | 2903881 A1 | 1/2008 |
| WO | WO-03092557 A2 | 11/2003 |

OTHER PUBLICATIONS

International Search Report and Written Opinion dated Jul. 20, 2010 for PCT/US2010/033705 filed May 5, 2010, claiming benefit of U.S. Appl. No. 12/436,225, filed May 6, 2009.

(Continued)

*Primary Examiner* — Ann Schillinger
(74) *Attorney, Agent, or Firm* — Schwegman Lundberg & Woessner, P.A.

(57) ABSTRACT

A system for replacing a hip joint can include a first acetabular cup formed of a first material and having a first inner diameter and a first thickness. A second acetabular cup can be formed of a second material and having a second inner diameter and a second thickness. A first femoral hip prosthesis can include a first femoral head that is alternately accommodated by either of the first or second acetabular cups. A bearing can be adapted to be interposed between the first femoral head and one of the first or second acetabular cups. The first and second inner diameters can be the same. The first thickness can be less than the second thickness. The first material can be distinct from the second material.

15 Claims, 4 Drawing Sheets

(56) References Cited

U.S. PATENT DOCUMENTS

| | | | |
|---|---|---|---|
| 5,549,691 A * | 8/1996 | Harwin | A61F 2/34 |
| | | | 623/22.34 |
| 5,549,692 A | 8/1996 | Hauser et al. | |
| 5,549,695 A | 8/1996 | Spotorno et al. | |
| 5,735,901 A | 4/1998 | Maumy et al. | |
| 6,290,726 B1 * | 9/2001 | Pope et al. | 623/22.15 |
| 6,811,569 B1 | 11/2004 | Afriat et al. | |
| 6,896,703 B2 | 5/2005 | Barbieri et al. | |
| 2003/0105529 A1 * | 6/2003 | Synder | A61F 2/34 |
| | | | 623/22.24 |
| 2004/0078083 A1 * | 4/2004 | Gibbs et al. | 623/22.17 |
| 2005/0171614 A1 | 8/2005 | Bacon | |
| 2006/0287733 A1 * | 12/2006 | Bonutti | A61F 2/0077 |
| | | | 623/20.3 |
| 2008/0255672 A1 * | 10/2008 | Gil | A61F 2/34 |
| | | | 623/22.28 |
| 2009/0093887 A1 * | 4/2009 | Walter | A61F 2/30721 |
| | | | 623/22.11 |

OTHER PUBLICATIONS

International Preliminary Report on Patentability and Written Opinion dated Nov. 17, 2011 for PCT/US2010/033705 filed May 5, 2010, claiming benefit of U.S. Appl. No. 12/436,225, filed May 6, 2009.

* cited by examiner

ACETABULAR CUP SYSTEM

FIELD

The present disclosure relates generally to a system and method for use in orthopedic surgery and, more particularly, to an acetabular cup system or kit, which includes a plurality of different sized acetabular cups formed from two different materials having different stiffnesses.

BACKGROUND

A natural hip joint may undergo degenerative changes due to a variety of etiologies. When such degenerative changes become so far advanced and irreversible, it may ultimately become necessary to replace a natural hip joint with a prosthetic hip. If the acetabulum needs repair, all remnants of articular cartilage may be removed from the acetabulum and an acetabular prosthesis which will accommodate the head or ball of the hip prosthesis may be affixed to the acetabulum.

The acetabular prosthesis can include an acetabular cup and a bearing that, in combination, cooperate with the head or ball of the hip prosthesis. One suitable material for such an acetabular cup is titanium. Titanium has the benefit of being biocompatible as well as elastic. Elasticity can be an important material characteristic as most acetabular cups need to deform slightly during press-fitting into a prepared acetabulum. However, because titanium is so elastic, the material generally needs to be a predetermined minimum thickness (e.g., about 3.5 mm or larger) in order to accommodate the loads in this area. This minimum thickness either requires the head of the femoral component to be smaller or additional reaming and bone removal to accommodate an acetabular cup having a larger outer diameter. In most cases however, reducing the size of the femoral head is unfavorable as it may increase the risk of dislocation. Moreover, it is desirable to keep reaming and bone removal at a minimum in order to maximize the amount of host bone in the acetabular socket for receipt of the acetabular cup.

SUMMARY

This section provides a general summary of the disclosure, and is not a comprehensive disclosure of its full scope or all of its features.

A system for replacing a hip joint can include a first acetabular cup formed of a first material and having a first inner diameter and a first thickness. A second acetabular cup can be formed of a second material and having a second inner diameter and a second thickness. A first femoral hip prosthesis can include a first femoral head that is alternately accommodated by either of the first or second acetabular cups. A bearing can be adapted to be interposed between the first femoral head and one of the first or second acetabular cups. The first and second inner diameters can be the same. The first thickness can be less than the second thickness. The first material can be distinct from the second material.

According to additional features, the first acetabular cup can have a first outer diameter. The second acetabular cup can have a second outer diameter. The first outer diameter can be less than the second outer diameter. The second material can be more flexible than the first material. In one example, the first material can be cobalt-chrome molybdenum and the second material can be titanium. The first and second acetabular cups can have substantially similar flexibility.

A related method can include preparing an acetabular socket of a hip joint. A size of the prepared acetabular socket can then be determined. One of the first or the second acetabular cups can be selected based on the determined size of the prepared acetabular socket. The selected first or second acetabular cup can be impacted into the acetabular socket. The first femoral hip prosthesis can be implanted, and the bearing can be positioned between the femoral head and the selected first or second acetabular cups.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description will be specifically directed toward a primary hip replacement procedure wherein a femoral hip prosthesis, an acetabular cup, and a bearing are implanted into the patient. It is appreciated however that the following teachings may also be applied to a surgical procedure for implanting other combinations of acetabular components. Moreover, the following teachings may also be applicable to a hip revision surgical procedure wherein a surgeon may be required to remove entirely or portions of a previously implanted hip prosthesis.

Figure 1:
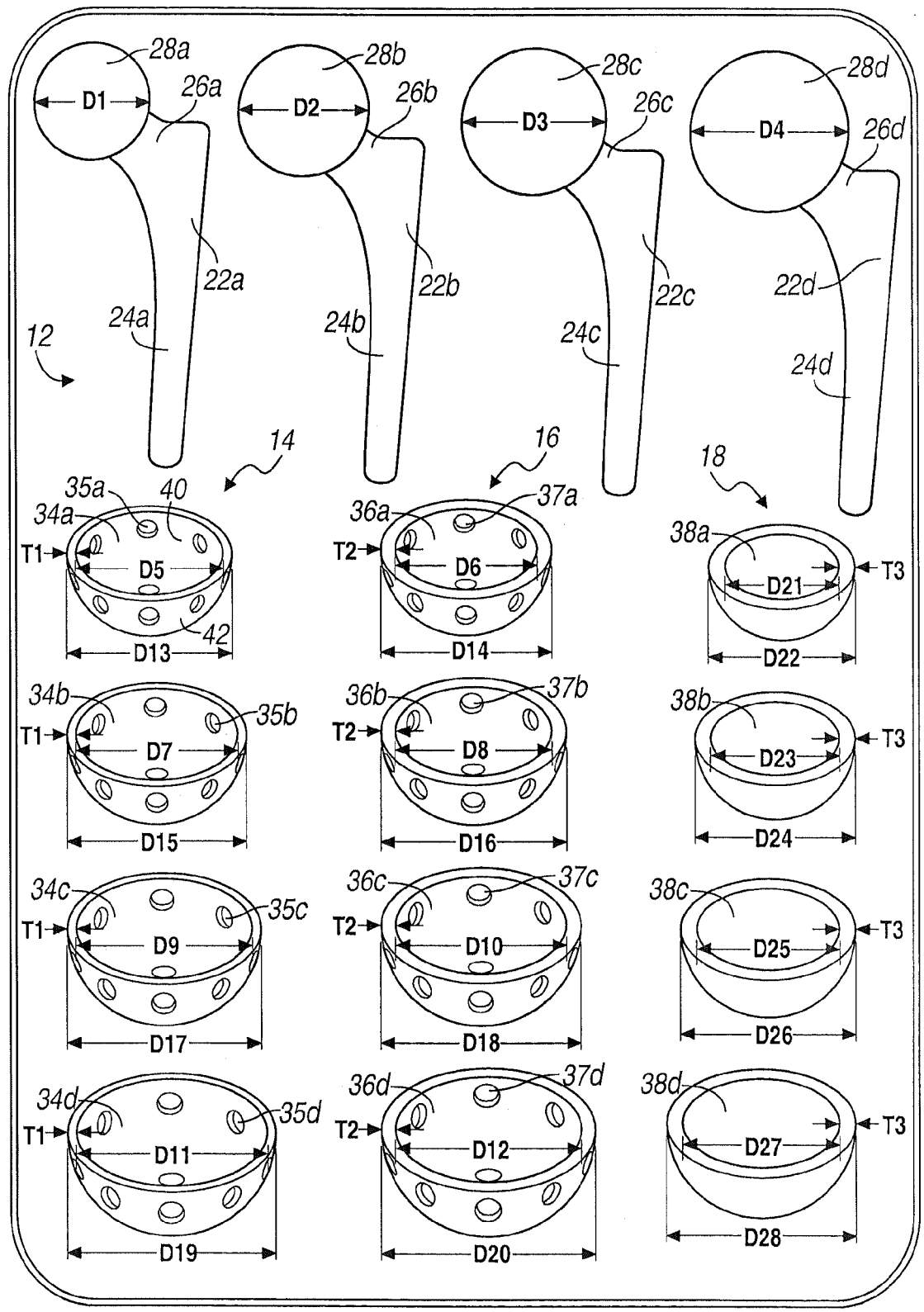
FIG. 1 is a perspective view of a system or kit for replacing a hip joint and including a plurality of femoral hip prostheses, a first set or plurality of acetabular cups, a second set or plurality of acetabular cups and a first set or plurality of bearings.
Figure 2:
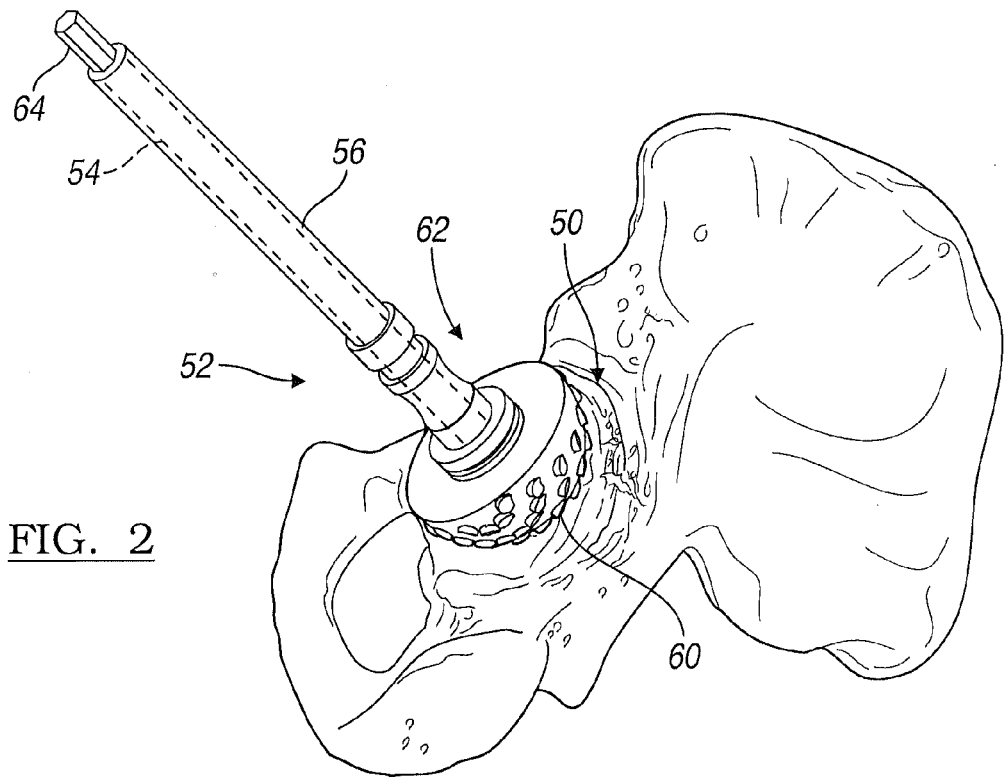
FIG. 2 is an anterior perspective view of an acetabulum being reamed by an exemplary reamer.

With initial reference to FIG. 1, a system or kit for use during a surgical hip replacement procedure is shown and generally identified at reference numeral 10. The kit 10 can generally include a plurality of femoral hip prostheses collectively referred to at reference numeral 12, a first set of acetabular cups collectively referred to at reference numeral 14, a second set of acetabular cups collectively referred to at reference numeral 16 and a set of bearings collectively referred to at reference numeral 18. The femoral hip prostheses 12 can include a first, second, third and fourth femoral hip prosthesis 22a, 22b, 22c and 22d, respectively. The first femoral hip prosthesis 22a can generally include a stem 24a, a neck 26a and a head 28a. The second femoral hip prosthesis 22b can generally include a stem 24b, a neck 26b and a head 28b. The third femoral hip prosthesis 22c can include a stem 24c, a neck 26c and a head 28c. The fourth femoral hip prosthesis 22d can include a stem 24d, a neck 26d and a head 28d. The heads 28a-28d each have a different diameter d1-d4, respectively. In one example, as will be described further below, the diameters d1-d4 can increase in size sequentially from the head 28a to the head 28d. The hip prostheses 12 can be modular having specific head, neck and stem configurations. The hip prosthesis 12 can also be monolithic.

The first set of acetabular cups 14 can generally include a first acetabular cup 34a, a second acetabular cup 34b, a third acetabular cup 34c and a fourth acetabular cup 34d. Each of the acetabular cups 34a-34d is formed of a first material and has a common thickness T1. In one example, the first material can be cobalt-chrome molybdenum. According to the present teachings, and as will be described further below, the inner diameter and the outer diameter of the first set of acetabular cups 14 is sequentially increased from the first acetabular cup 34a through the fourth acetabular cup 34d. The first set of acetabular cups 14 can each include a plurality of passages 35a-35d formed therethrough.

The second set of acetabular cups 16 can generally include a first acetabular cup 36a, a second acetabular cup 36b, a third acetabular cup 36c and a fourth acetabular cup 36d. Each of the acetabular cups 36a-36d is formed of a second material and has a thickness T2. In one example, the second material can be titanium. According to the present teachings, and as will be described further below, the inner diameter and the outer diameter of the second set of acetabular cups 16 is sequentially increased from the first acetabular cup 36a through the fourth acetabular cup 36d. Each of the acetabular cups of the second set of acetabular cups 16 includes a plurality of optional screw receiving passages 37a-37d. Any or all of the first and second sets of acetabular cups 14 and 16 can include an outer layer of porous material to enhance bony ingrowth.

The first set of bearings 18 can generally include a first bearing 38a, a second bearing 38b, a third bearing 38c and a fourth bearing 38d. Each of the bearings 38a-38d has a common thickness T3. The bearings 18 can have any suitable configuration, such as constrained bearings, high-wall bearings or other bearing configurations.

According to the teachings of the present disclosure, in the present example, each component in the kit 10 is compatible with other components of the kit 10 having a similar suffix. In other words, in the present example, the femoral hip prosthesis 22a can cooperate with the bearing 38a and either one of the acetabular cups 34a or 36a. Likewise, the femoral hip prosthesis 22b can be used with the bearing 38b and either of the acetabular cups 34b or 36b. The femoral hip prosthesis 22c can be used with the bearing 38c and either of the acetabular cups 34c or 36c. The femoral hip prosthesis 22d can be used with the bearing 38d and either of the acetabular cups 34d or 36d.

Exemplary dimensions of the components of the kit 10 will now be described for exemplary purposes. It is appreciated however that the dimensions may be changed without departing from the scope of the present disclosure. As used herein the phrase "the same" is used to denote an identical or substantially identical dimension within a tolerance. In one example, the dimensions can be the same within a tolerance of about 0.25 mm. All of the acetabular cups 34a-34d and 36a-36d have a hemispherical shape and include an inner bearing engaging surface and an outer bone engaging surface 40 and 42, respectively (only identified on acetabular cup 34a for clarity). Various diameters can be provided for the acetabular cups 34a-36d as described below. In general, an inner diameter D5 of the acetabular cup 34a is the same or substantially the same as an inner diameter D6 of the acetabular cup 36a. Likewise, an inner diameter D7 of the acetabular cup 34b is the same or substantially the same as an inner diameter D8 of the acetabular cup 36b. The inner diameter D9 of the acetabular cup 34c is the same or substantially the same as the inner diameter D10 of the acetabular cup 36c. The inner diameter D11 of the acetabular cup 36d is the same or substantially the same as the inner diameter D12 of the acetabular cup 36d.

In one example, the inner diameters D5 and D6 can be 41 mm, the inner diameters D7 and D8 can be 45 mm, the inner diameters D9 and D10 can be 49 mm and the diameters D11 and D12 can be 53 mm. In general, the outer diameters D13-D20 sequentially increase by 2 mm. Thus, the acetabular cup 34a can have an outer diameter D13 of 46 mm. The acetabular cup 36a can have an outer diameter D14 that is 48 mm. The acetabular cup 34b can have an outer diameter D15 that is 50 mm. The acetabular cup 36b can have an outer diameter D16 that is 52 mm. The acetabular cup 34c can have an outer diameter D17 that is 54 mm. The acetabular cup 36c can have an outer diameter D18 that is 56 mm. The acetabular cup 34d can have an outer diameter D19 that is 58 mm. The acetabular cup 36d can have an outer diameter D20 that is 60 mm. In one example, the thickness T1 is 2.5 mm and the thickness T2 is 3.5 mm.

In the present example, the bearing 38a has an inner diameter D21 of 32 mm and an outer diameter D22 of 41 mm. The bearing 38b has an inner diameter D23 of 36 mm and an outer diameter D24 of 45 mm. The bearing 38c has an inner diameter D25 of 40 mm and an outer diameter D26 of 49 mm. The bearing 38d has an inner diameter D27 of 44 mm and an outer diameter D28 of 53 mm. In this example, the thickness T3 of each of the bearings 38a-38d can be 4.5 mm.

The diameter of the head 28a of the femoral hip prosthesis 22a can be 32 mm. The diameter of the head 28b of the femoral hip prosthesis 22b can be 36 mm. The diameter D3 of the head 28c of the femoral hip prosthesis 22c can be 40 mm. The diameter D4 of the head 28d of the femoral hip prosthesis 22d can be 44 mm. Again it will be appreciated that the dimensions set forth herein are merely exemplary. Furthermore, the dimensions may be approximate. Again, inner diameters of various acetabular cups 14, 16 that are described as being the same or substantially the same are so within specific tolerances.

With additional reference now to FIGS. 2-5, an exemplary method for using the kit 10 to replace a hip joint according to one example of the present teachings will now be described. Initially, an acetabulum 50 can be reamed, such as with a reamer 52. The exemplary reamer 52 can comprise a reamer drive shaft 54 that is rotatably supported within a cannulated shaft 56. A cutting member 60 can be selectively coupled at a distal end 62 of the reamer drive shaft 54. A mating structure 64 can be provided at a proximal end of the reamer drive shaft 54. A driver (not shown) may be operably coupled with the mating structure 64 to impart rotational force through the reamer drive shaft 54 to the cutting member 60. The acetabulum 50 may be generally hemispherically reamed until concentric removal of all acetabular cartilage and/or bone cement and portions of host bone if necessary (e.g., such as during a revision procedure) is achieved. Once the acetabulum 50 has been appropriately reamed, trial gauges (not shown), which are well known in the art, may be used to determine the size of the reamed acetabulum 50. A corresponding outer diameter of a suitable acetabular cup (e.g., a corresponding acetabular cup from the first and second sets of acetabular cups 14 and 16) is then known.

Figure 3:
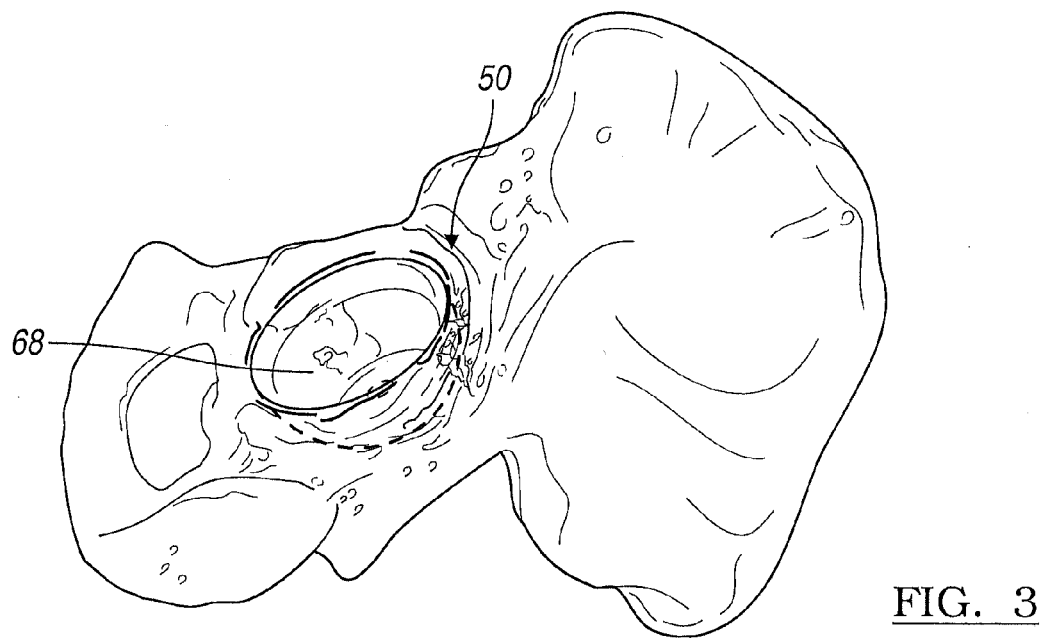
FIG. 3 is an anterior perspective view of a reamed acetabular socket subsequent to reaming.

As illustrated in FIG. 3, the acetabulum 50 is shown having a reamed acetabular socket 68. Again, it can be desirable to leave as much host bone from the acetabulum 50 in place. As explained above, the first set of acetabular cups 14 are all formed by cobalt-chrome molybdenum and have a thickness of 2.5 mm. The second set of acetabular cups 16 are all formed of titanium and have a thickness of 3.5 mm. As is known, the stiffness of cobalt-chrome molybdenum per unit thickness is higher than titanium. Moreover, titanium has a higher flexibility per unit thickness than cobalt-chrome molybdenum. Because each acetabular cup 34a-34d of the first set of acetabular cups 14 is thinner than each acetabular cup 36a-36d of the second set of acetabular cups 16 (2.5 mm vs. 3.5 mm), the stiffness of an acetabular cup 34a-34d of the first set of acetabular cups 14 relative to a corresponding acetabular cup 36a-36d of the second set of acetabular cups 16 is the same or substantially the same. In this way, a surgeon 70 (FIG. 4) is able to achieve a desired stiffness utilizing any of the acetabular cups from the first or second sets of acetabular cups 14 and 16 to attain a desired press-fit relationship into the reamed acetabular socket 68 of patient 72.

Figure 4:
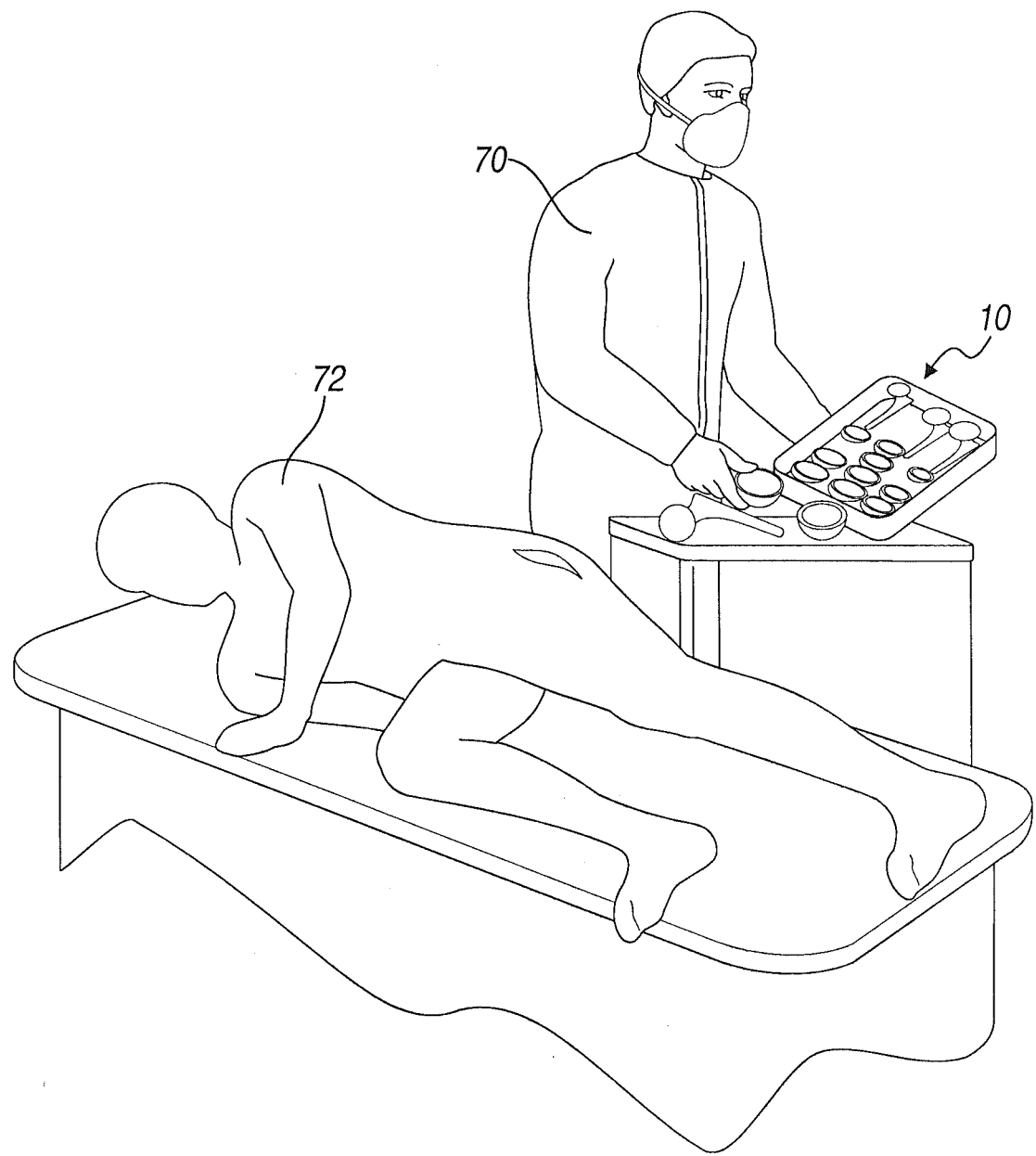
FIG. 4 is a perspective environmental view of a surgeon determining suitable components of the kit of FIG. 1 based on measurements of the reamed acetabular socket of FIG. 3.

With continued reference now to FIG. 4, by initially starting with cobalt-chrome molybdenum, a thinner 2.5 mm thickness acetabular cup (such as acetabular cup 34a) can be used to accommodate a first femoral head size (i.e., D1 of femoral head 28a). When the surgeon 70 may require the next larger size outer diameter acetabular cup (such as the acetabular cup 36a), the same femoral head 28a can be used since the inner diameter (i.e., D5 vs. D6) stays the same and the material of the acetabular cup changes to titanium having a thickness of 3.5 mm (and consequently the acetabular cup outer diameter increases by 2 mm). If the surgeon 70 determines that the next larger size femoral head (i.e., femoral head 28b) should be used, the surgeon 70 can select the cobalt-chrome molybdenum acetabular cup 34b having the thickness of 2.5 mm. If it is determined that the next size larger outer diameter acetabular cup is required, the surgeon 70 can select the titanium acetabular cup 36b having a thickness of 3.5 mm. Again, it is appreciated that the femoral hip prosthesis 22b having the head 28b can be used for either of the acetabular cups 34b or 36b because the inner diameters D7 vs. D8 are the same or substantially the same. As can be appreciated, the surgeon 70 can make similar decisions as to whether other acetabular cups, such as 34c-36d or others may be particularly suited for a given patient 72. Nevertheless, the kit 10 can be used by the surgeon 70 to minimize host bone loss without having to compromise head size of the femoral hip prosthesis while at the same time providing the surgeon 70 with the desired acetabular cup flexibility during implantation. Furthermore, with the kit 10, a larger diameter head can be used 50% of the time as a cobalt-chrome molybdenum cup can be used having the same outer diameter as a comparable titanium cup while offering a larger inner diameter that accommodates the larger diameter head. As used herein, the term "kit" or "system" is used to denote a collection of readily available components (i.e., acetabular cups, bearings and/or femoral hip prostheses) available for a surgeons easy selection. The collection of readily available components can be grouped or arranged in any manner that provides the surgeon with comprehensive access and ease of identification. In this way, each of the components may be prepackaged individually in sterile containers while still being offered as a collective kit or set of components.

Figure 5:
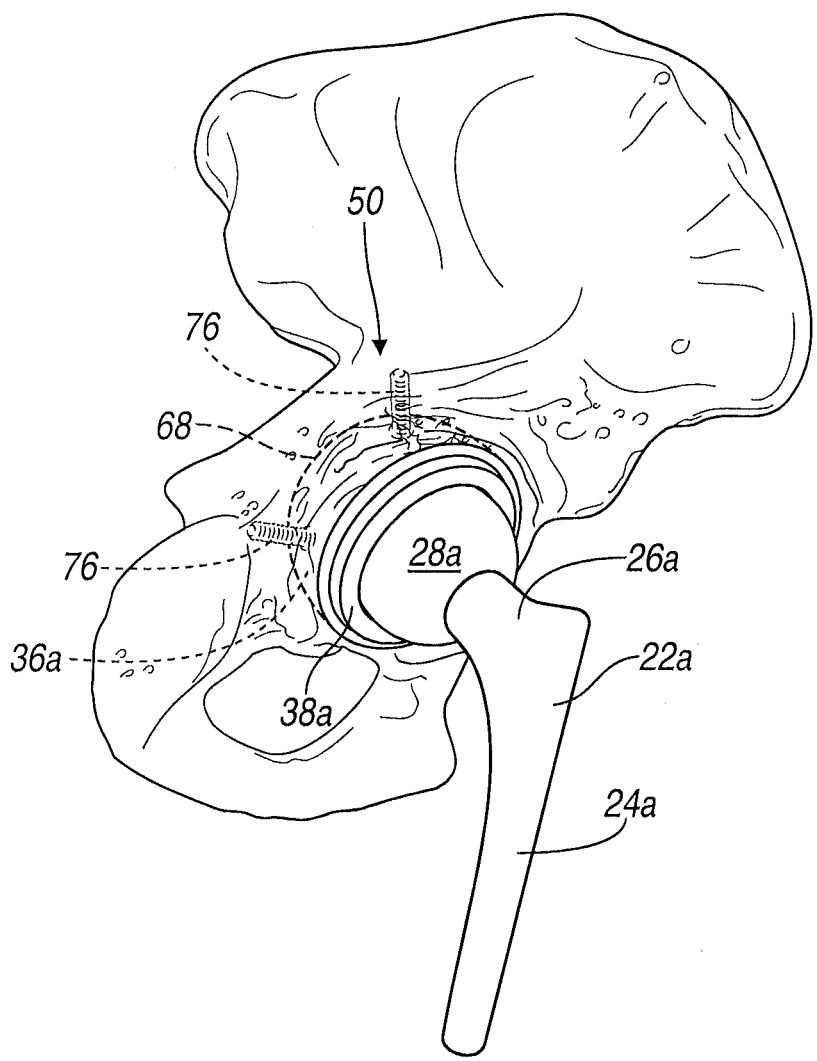
FIG. 5 is an anterior view of a femoral hip prosthesis, a bearing and an acetabular cup selected from the kit and shown in an implanted position in the acetabular socket.

Turning now to FIG. 5, an acetabular cup 36a is shown implanted into the reamed acetabular socket 68. The cup 36a can be implanted by any suitable method. According to one such method, an impacting instrument (not shown) may be used to properly position the acetabular cup 36a. In one example, the impacting instrument may be threadably secured to an apical hole (not specifically shown) of the acetabular cup 36a. Once the orientation of the acetabular cup 36a is acceptable, the inserting instrument may be solidly impacted to fully seat (or press-fit) the acetabular cup 36a into the acetabular socket 68, such that firm rim fixation is achieved. Once the acetabular cup 36a has been solidly impacted, the inserting instrument may be carefully removed from the acetabular cup 36a.

A plurality of bone screw holes (not specifically shown) may be bored into the acetabulum 50 while aligning with existing holes 37a already formed in the acetabular cup 36a. Once the bone screw holes have been formed in the acetabulum 50, as is also known in the art, a depth gauge (not shown) may be used to determine the length of the fixation screws. With the length of the screws determined, a fixation screw or multiple fixation screws 76 may be advanced through the respective holes 37a in the acetabular cup 36a and driven into the screw holes in the acetabulum 50. In other examples, the acetabular cup 36a additionally or alternatively may be cemented into the acetabulum 50.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for replacing a hip joint, the system comprising:
   a first femoral hip prosthesis including a first femoral head shaped to have a first femoral head outer diameter;
   a first bearing shaped to have:
      a first bearing inner diameter the same as the first femoral head outer diameter, and a first bearing outer diameter;
   a first acetabular cup configured to cooperate with the first bearing and the first femoral head, the first acetabular cup being formed of a first material and shaped to have:
      an inner diameter the same as the first bearing outer diameter; and
      a first outer diameter; and
   a second acetabular cup configured to cooperate with the first bearing and the first femoral head, the second acetabular cup being formed of a second material having a lower stiffness per unit thickness than the first material, and shaped to have:
      an inner diameter the same as the first bearing outer diameter; and
      a second outer diameter greater than the first outer diameter, the second outer diameter being selected so that the second acetabular cup has a stiffness that matches a stiffness of the first acetabular cup.

2. The system of claim 1, wherein:
the first material is cobalt-chrome molybdenum; and
the second material is titanium.

3. The system of claim 1, further comprising:
a second femoral hip prosthesis including a second femoral head shaped to have a second femoral head outer diameter different from the first femoral head outer diameter;
a second bearing shaped to have:
a second bearing inner diameter the same as the second femoral head outer diameter, and a second bearing outer diameter;
a third acetabular cup configured to cooperate with the second bearing and the second femoral head, the third acetabular cup being formed of the first material and shaped to have:
an inner diameter the same as the second bearing outer diameter; and
a third outer diameter; and
a fourth acetabular cup configured to cooperate with the second bearing and the second femoral head, the fourth acetabular cup being formed of the second material and shaped to have:
an inner diameter the same as the second bearing outer diameter; and
a fourth outer diameter greater than the third outer diameter.

4. The system of claim 1, further comprising:
a first plurality of acetabular cups formed of the first material,
the first plurality of acetabular cups being shaped to have sequentially increasing first inner diameters and sequentially increasing first outer diameters,
each first inner diameter and first outer diameter defining a first cup thickness,
the first cup thicknesses all being equal to a first thickness value; and
a second plurality of acetabular cups formed of the second material, each of the acetabular cups in the second plurality of acetabular cups corresponding to one of the acetabular cups in the first plurality of acetabular cups,
the second plurality of acetabular cups being shaped to have sequentially increasing second inner diameters and sequentially increasing second outer diameters,
each second inner diameter equal to the first inner diameter of the corresponding acetabular cup in the first plurality of acetabular cups,
each second inner diameter and second outer diameter defining a second cup thickness,
the second cup thicknesses all being equal to a second thickness value; and
the second thickness value being greater than the first thickness value.

5. The system of claim 4, wherein:
the acetabular cups in the first plurality have the same stiffness;
the acetabular cups in the second plurality have the same stiffness; and
the second thickness value is selected so that the first and second pluralities of acetabular cups have the same stiffness.

6. The system of claim 5 wherein each pair of corresponding first and second acetabular cups is adapted to alternately accommodate a common femoral head of a femoral hip prosthesis.

7. A system for replacing a hip joint, the system comprising:
a first plurality of acetabular cups formed of a first material,
the first plurality of acetabular cups being shaped to have sequentially increasing first inner diameters and sequentially increasing first outer diameters,
each first inner diameter and first outer diameter defining a first cup thickness, the first cup thicknesses all being equal to a first thickness value; and
a second plurality of acetabular cups formed of a second material having a lower stiffness per unit thickness than the first material,
the second plurality of acetabular cups being shaped to have sequentially increasing second inner diameters and sequentially increasing second outer diameters,
each second inner diameter being equal to a corresponding first inner diameter,
each second inner diameter and second outer diameter defining a second cup thickness,
the second cup thicknesses all being equal to a second thickness value,
the second thickness value being greater than the first thickness value,
the second thickness value being selected so that the first and second pluralities of acetabular cups all have the same stiffness.

8. The system of claim 7, further comprising a plurality of femoral hip components, each femoral hip component configured to alternatively cooperate with one acetabular cup of the first plurality and one acetabular cup of the second plurality.

9. The system of claim 7, wherein:
the first material is cobalt-chrome molybdenum; and
the second material is titanium.

10. The system of claim 7, wherein the first inner diameters, the first outer diameters, the second inner diameters, and the second outer diameters increment by 2 mm.

11. The system of claim 7, wherein:
the first thickness value is 2.5 mm; and
the second thickness value is 3.5 mm.

12. A system for replacing a hip joint, the system comprising:
a plurality of femoral heads shaped to have sequentially increasing femoral head outer diameters;
a plurality of bearings shaped to have sequentially increasing bearing inner diameters and sequentially increasing bearing outer diameters, each bearing corresponding to a femoral head in the plurality of femoral heads, and for each pair of corresponding bearings and femoral heads, the
bearing inner diameter is the same as the femoral head outer diameter;
a first plurality of acetabular cups, each of the first plurality of acetabular cups being configured to correspond to and cooperate with one of the plurality of bearings and one of the plurality of femoral heads, the acetabular cups in the first plurality being formed of a first material and shaped to have:
sequentially increasing first inner diameters, each of the first inner diameters being the same as the bearing outer diameter of the corresponding bearing,
sequentially increasing first outer diameters,
each first inner diameter and first outer diameter defining a first cup thickness,
the first cup thicknesses all being equal to a first thickness value; and
a second plurality of acetabular cups, each of the second plurality of acetabular cups being configured to correspond to and cooperate with one of the plurality of bearings and one of the plurality of femoral heads, the acetabular cups in the second plurality being formed of a second material having a lower stiffness per unit thickness than the first material, the second plurality of acetabular cups being shaped to have:

sequentially increasing second inner diameters, each of the second inner diameters being the same as the bearing outer diameter of the corresponding bearing, sequentially increasing second outer diameters, each second inner diameter and second outer diameter defining a second cup thickness, the second cup thicknesses all being equal to a second thickness value, the second thickness value being greater than the first thickness value, the second thickness value being selected so that the first and second pluralities of acetabular cups all have the same stiffness.

13. The system of claim 12, wherein the first inner diameters, the first outer diameters, the second inner diameters, and the second outer diameters sequentially increase by 2 mm.

14. The system of claim 12, wherein:
the first thickness value is 2.5 mm; and
the second thickness value is 3.5 mm.

15. The system of claim 14, wherein:
the first material is cobalt-chrome molybdenum; and
the second material is titanium.

* * * * *